US011367521B1

(12) United States Patent
Neumann

(10) Patent No.: US 11,367,521 B1
(45) Date of Patent: Jun. 21, 2022

(54) SYSTEM AND METHOD FOR GENERATING A MESODERMAL OUTLINE NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,166

(22) Filed: Dec. 29, 2020

(51) Int. Cl.
*G16H 20/60* (2018.01)
*G16H 50/70* (2018.01)
(Continued)

(52) U.S. Cl.
CPC ............. *G16H 20/60* (2018.01); *G16H 10/60* (2018.01); *G16H 50/20* (2018.01); *G16H 50/30* (2018.01); *G16H 50/70* (2018.01); *G16H 70/60* (2018.01)

(58) Field of Classification Search
CPC ........ G16H 10/60; G16H 50/20; G16H 50/70; G16H 20/60; G16H 50/30; G16H 20/00; G16H 70/60
(Continued)

(56) References Cited

U.S. PATENT DOCUMENTS

| 2006/0062859 A1 | 3/2006 | Blum |
| 2007/0264673 A1 | 11/2007 | Wild |
| 2008/0221932 A1 | 9/2008 | Kane |

(Continued)

FOREIGN PATENT DOCUMENTS

| WO | WO-9952050 A1 * | 10/1999 | ........... G06F 15/025 |
| WO | 2005103300 A2 | 11/2005 | |

(Continued)

OTHER PUBLICATIONS

Hui Yang; On building a quantitative food-disease-gene network; International Society for Computers and Their Applications. 2nd International Conference on Bioinformatics and Computational Biology (BICoB-2010) : 92-7;iv+210. International Society for Computers and Their Applications. (2010) (Year: 2010).*

(Continued)

*Primary Examiner* — Hiep V Nguyen
(74) *Attorney, Agent, or Firm* — Caldwell Intellectual Property Law; Katherine Rubino

(57) ABSTRACT

A system and method for generating a mesodermal outline nourishment program comprises a computing device configured to obtain an undifferentiated connective tissue workup as a function of a connective tissue system, determine a mesodermal outline as a function of the undifferentiated connective tissue workup, wherein determining comprises obtaining a mesodermal group as a function of a connective database, and determining the mesodermal outline as a function of the mesodermal group and undifferentiated connective tissue workup using a mesodermal machine-learning model, generate an outline signature as a function of the mesodermal outline, wherein generating comprises receiving a normal range as a function of a mesodermal guideline, and generating the outline signature as a function of the normal range and mesodermal outline using a signature machine-learning model, identify an edible as a function of the outline signature, and output a nourishment program as a function of the edible.

20 Claims, 7 Drawing Sheets

(51) Int. Cl.
  *G16H 10/60* (2018.01)
  *G16H 70/60* (2018.01)
  *G16H 50/30* (2018.01)
  *G16H 50/20* (2018.01)

(58) Field of Classification Search
  USPC .......................................................... 705/2
  See application file for complete search history.

(56) References Cited

U.S. PATENT DOCUMENTS

| | | |
|---|---|---|
| 2011/0189161 A1 | 8/2011 | Blum |
| 2012/0041683 A1* | 2/2012 | Vaske ............... G16B 5/20 702/19 |
| 2013/0157233 A1 | 6/2013 | Leville |
| 2013/0261183 A1 | 10/2013 | Bhagat |
| 2015/0369824 A1 | 12/2015 | Dervieux |
| 2017/0286622 A1 | 10/2017 | Cox |
| 2020/0027181 A1 | 1/2020 | Ohnemus |
| 2020/0049705 A1 | 2/2020 | James |
| 2020/0321115 A1 | 10/2020 | Neumann |
| 2020/0321119 A1 | 10/2020 | Neumann |

FOREIGN PATENT DOCUMENTS

| | | | |
|---|---|---|---|
| WO | WO-2009033746 A2 * | 3/2009 | ............... A61P 3/06 |
| WO | WO-2012037456 A1 * | 3/2012 | ............. A61P 37/02 |
| WO | 2015004266 A1 | 1/2015 | |
| WO | 2016141127 A1 | 9/2016 | |
| WO | 2019087196 A1 | 5/2019 | |

OTHER PUBLICATIONS

Nutrients. Oct. 2020; 12(10): 3140.Published online Oct. 14, 2020. doi: 10.3390/nu12103140 Retrieved from website: https://www.ncbi.nlm.nih.gov/pmc/articles/PMC7602401/Title: Statistical and Machine-Learning Analysesin Nutritional Genomics Studies Date: Oct. 14, 2020 By: Leila Khorraminezhad.

Nutr Res Rev. Jun. 2017;30(1):118-137. doi: 10.1017/S0954422417000026. Retrieved from website: https://pubmed.ncbi.nlm.nih.gov/28294088/Title: An update on diet and nutritional factors in systemic lupus erythematosus management Date: Jun. 2017 By: Marina Aparicio-Soto.

Front. Immunol., Jul. 22, 2020 https://doi.org/10.3389/fimmu.2020.01477. Retrieved from website: https://www.frontiersin.org/articles/10.3389/fimmu.2020.01477/full Title: Immunomodulatory Effects of Diet and Nutrients in Systemic Lupus Erythematosus (SLE): A Systematic Review Date: Jul. 22, 2020 By: Md Asiful Islam.

Retrieved from website: https://onlinelibrary.wiley.eom/doi/abs/10.1002/9781118930458.ch7 Title:Nutrigenomics, Inflammaging, and Osteoarthritis Date: Aug. 14, 2015 By: Ali Mobasheri.

* cited by examiner

US 11,367,521 B1

SYSTEM AND METHOD FOR GENERATING A MESODERMAL OUTLINE NOURISHMENT PROGRAM

FIELD OF THE INVENTION

The present invention generally relates to the field of artificial intelligence. In particular, the present invention is directed to a system and method for generating a mesodermal outline nourishment program.

BACKGROUND

Current edible suggestion systems do not account for ocular measurements of an individual. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect a system for generating a mesodermal outline nourishment program comprises a computing device, the computing device configured to obtain at least an undifferentiated connective tissue workup as a function of a connective tissue system, determine a mesodermal outline as a function of the undifferentiated connective tissue workup, wherein determining comprises obtaining a mesodermal group as a function of a connective database, and determining the mesodermal outline as a function of the mesodermal group and undifferentiated connective tissue workup using a mesodermal machine-learning model, generate an outline signature as a function of the mesodermal outline, wherein generating comprises receiving a normal range as a function of a mesodermal guideline, and generating the outline signature as a function of the normal range and mesodermal outline using a signature machine-learning model, identify an edible as a function of the outline signature, and output a nourishment program of a plurality of nourishment programs as a function of the edible.

In another aspect a method for generating a mesodermal outline nourishment program comprises obtaining, by a computing device, at least an undifferentiated connective tissue workup as a function of a connective tissue system, determining, by the computing device, a mesodermal outline as a function of the undifferentiated connective tissue workup, wherein determining comprises obtaining a mesodermal group as a function of a connective database, and determining the mesodermal outline as a function of the mesodermal group and undifferentiated connective tissue workup using a mesodermal machine-learning model, generating, by the computing device, an outline signature as a function of the mesodermal outline, wherein generating comprises receiving a normal range as a function of a mesodermal guideline, and generating the outline signature as a function of the normal range and mesodermal outline using a signature machine-learning model, identifying, by the computing device, an edible as a function of the outline signature, and outputting, by the computing device, a nourishment program of a plurality of nourishment programs as a function of the edible.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a mesodermal outline nourishment program. In an embodiment, this disclosure may obtain at least an undifferentiated connective tissue workup as a function of a connective tissue system. Aspects of the present disclosure can be used to determine a mesodermal outline as a function of the undifferentiated connective tissue workup. This is so, at least in part, because this disclosure uses a machine-learning model. Aspects of the present disclosure can be used to generate an outline signature. Aspects of the present disclosure can also be used to identify an edible as a function of the outline signature. Aspects of the present disclosure allow for outputting a nourishment program as a function of the edible. Exemplary embodiments illustrating aspects of the present disclosure are described below in the context of several specific examples.

Figure 1:
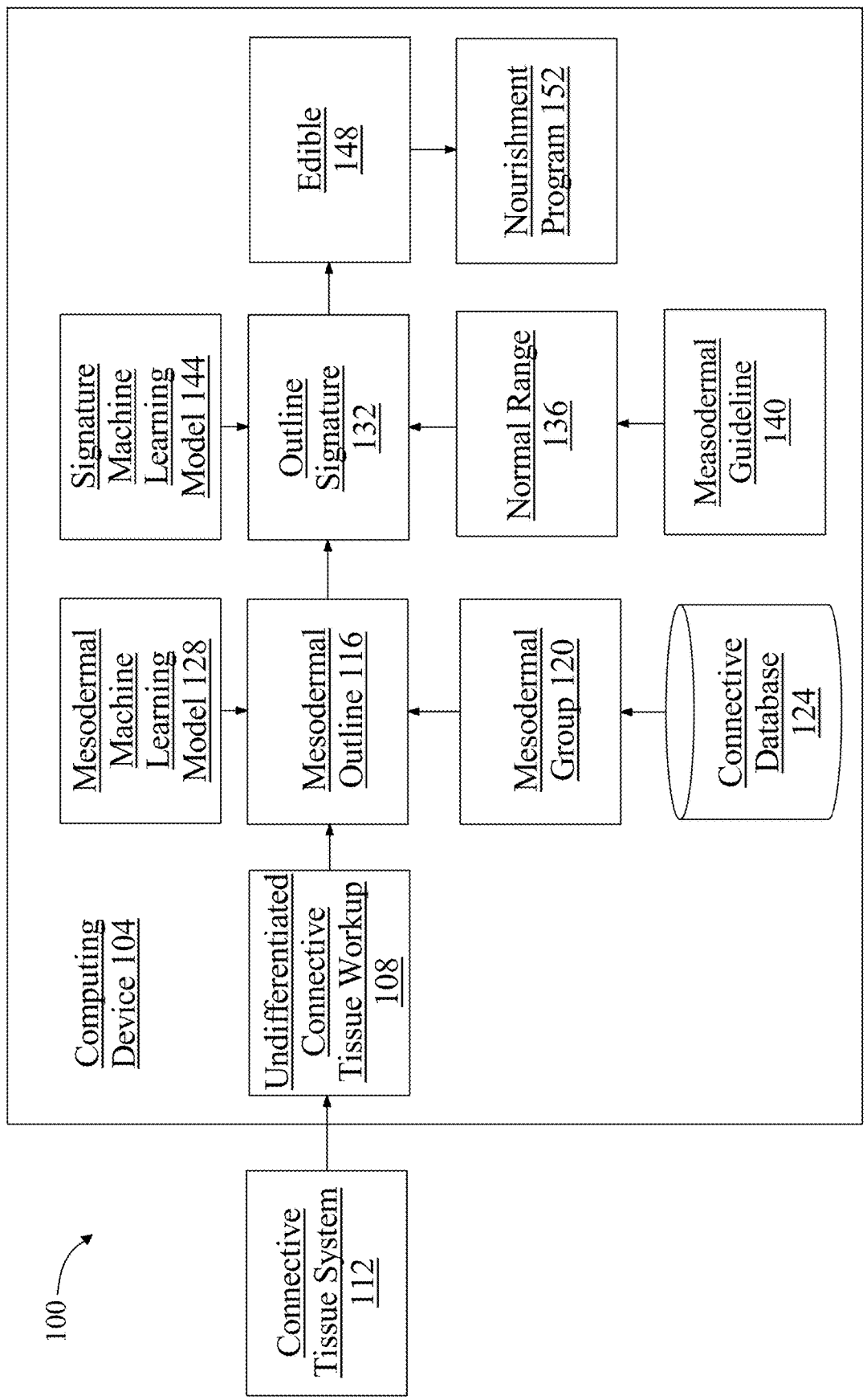
FIG. 1 is a block diagram illustrating an exemplary embodiment of a system for generating a mesodermal outline nourishment program.

Referring now to FIG. 1, an exemplary embodiment of a system 100 for generating a mesodermal outline nourishment program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains at least an undifferentiated connective tissue workup 108. As used in this disclosure an "undifferentiated connective tissue workup" is a result of one or more analysis techniques that represents a health status of a user's connective tissue system. Undifferentiated connective tissue workup 108 may include without limitation, a complete blood count, erythrocyte sedimentation rate, c-reactive protein count, urinalysis, microscopic analysis, serum creatine count, rheumatoid factor analysis, antinuclear antibodies analysis, immunofluorescence assay, enzyme-linked immunosorbent assay, creatine kinase analysis, aldolase analysis, completement components analysis, thyroid-stimulating hormone analysis, anti-cyclic citrullinated peptide analysis, anti-Ro/S SA analysis, Anti-La/SSB analysis, Anti-Smith analysis, Anti-U1-RNP analysis, Anti-Jo1 analysis, Anti-Mi2 analysis, topoisomerase antibody analysis, Anti cardiolipins analysis, Anti-beta-2 glycoprotein 1 analysis, Lupus anticoagulant analysis, Anti-Ku analysis, Rapid plasma regain analysis, Vitamin D analysis, and the like thereof. Undifferentiated connective tissue workup 108 may include a biological sample analysis. As used in this disclosure a "biological sample" is one or more biological specimens collected from an individual. Biological sample may include, without limitation, exhalate, blood, sputum, urine, saliva, feces, semen, and other bodily fluids, as well as tissue. Undifferentiated connective tissue workup 108 may relate to the analysis of one or more biomarkers, wherein biomarkers are molecules and/or chemicals that at least identify the health status of a user's connective tissue system. As a non-limiting example biomarkers may include, alkaline phosphatase, bone-specific alkaline phosphatase, procollagen type 1 amino-terminal propeptide, serum, urine C-terminal telopeptide, urine N-terminal telopeptide, Anti-ScL-70, Anticentromere, Anti-RNA polymerase, Anti-RNA polymerase III, Antigibrillarin, Anti-PM-Scl, Anti-Th/To, von Willebrand factor, Adhesion molecules, VEGFm, Type III procollagen peptides, TGF-B, CTGF, Cartilage oligomeric matrix protein, Endothelian-1, YKL-40, and the like thereof. As a further non-limiting example undifferentiated connective tissue workup 108 may include collecting, storing, and/or calculating one or more lights, voltages, currents, sounds, chemicals, pressures, and the like thereof that are associated with a connective tissue system. Undifferentiated connective tissue workup 108 is obtained as a function of a connective tissue system 112. As used in this disclosure, a "connective tissue system" is a tissue system consisting that is found in between other tissues everywhere in a user's body. As a non-limiting example connective tissue system 112 may include tissue derived from the mesoderm, the meninges, elastic fibers, collagenous fibers, fibroblasts, adipocytes, macrophages, mast cells, leukocytes, areolar tissue, adipose tissue, fibrous tissue, blood, osseous tissue, hyaline cartilage, and the like thereof.

Still referring to FIG. 1, computing device 104 obtains undifferentiated connective tissue workup 108 as a function of receiving a mesodermal diagnostic input. As used in this disclosure, a "mesodermal diagnostic input" is datum of connective tissue analysis information that is obtained from one or more informed advisors. As a non-limiting example mesodermal diagnostic input may include a skin rash, swelling of joints, serositis, seizures, psychosis, fever, fatigue, myalgia, myositis, alopecia, dry eyes, dry mouth, vasculitic lesions, edema, cyanosis, and the like thereof. As used in this disclosure, a "informed advisor" is an individual that is skilled in a particular area relating to the study of connective tissues. As a non-limiting example an informed advisor may include a medical professional who may assist and/or participate in the medical treatment of an individual's connective tissue system. An informed advisor may include rheumatologists, dermatologists, internists, general practitioners, neurologists, pulmonologists, nephrologists, family physicians, and the like thereof.

Still referring to FIG. 1, computing device 104 determines a mesodermal outline 116 as a function of undifferentiated connective tissue workup 108. As used in this disclosure, a "mesodermal outline" is a profile of the connective tissue system health status, wherein a health status is a relative level of wellness and illness of the connective tissue system. As a non-limiting example, mesodermal outline 116 may include a connective tissue system health status of binding and supporting surround organs and/or tissues. As a further non-limiting example, mesodermal outline 116 may include a connective tissue system health status of protecting surrounding organs and/or tissues. As a further non-limiting example, mesodermal outline 116 may include a connective tissue system health status of insulating surrounding organs and/or tissues. As a further non-limiting example, mesodermal outline 116 may include a connective tissue health status of transporting substances within the body of the user. Computing device 104 determines mesodermal outline 116 by obtaining a mesodermal group 120. As used in this disclosure, a "mesodermal group" is a group of similar connective tissue types based on the structure and/or function of the connective tissue, as described below in detail, in reference to FIG. 2. As a non-limiting example, mesodermal group 120 may include a blood group, bone group, connective tissue proper group, special connective tissue group, cartilage group, and the like thereof. Mesodermal group 120 is obtained as a function of a connective database 124. As used in this disclosure, a "connective database" is a database containing one or more mesodermal groups, as described below in detail, in reference to FIG. 4. As a non-limiting example, connective database 124 may include a peer review tableset, informed advisor associations tableset, and/or medical website tableset. Connective database 124 may provide mesodermal group as a function of one or more similarity parameters associated with undifferentiated connective tissue workup 108. For example, computing device 104 may obtain a bone group from connective database 124 as a function of a biomarker of osteoblasts from bone tissue. Connective database 124 may output mesodermal group 120 such that a location and/or group of connective tissues and/or organs may be identified.

Still referring to FIG. 1, computing device 104 determines mesodermal outline 116 as a function of mesodermal group 120 and undifferentiated connective tissue workup 108 using a mesodermal machine-learning model 128. As used in this disclosure, a "mesodermal machine-learning model" is a machine-learning model configured to produce mesodermal outline 116 as an output given mesodermal group 120 and undifferentiated connective tissue workup 108 as inputs; this is in contrast to a non-machine learning software program where the commands to be executed are determined in advance by a user and written in a programming language. Mesodermal machine-learning model 128 may include one or more mesodermal machine-learning processes such as supervised, unsupervised, or reinforcement machine-learning processes that computing device 104 and/or a remote device may or may not use in the determination of mesodermal outline 116. As used in this disclosure, a "remote device" is an external device to computing device 104. Mesodermal machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train mesodermal machine-learning process as a function of a mesodermal training set. As used in this disclosure, a "mesodermal training set" is a training set that correlates a mesodermal group and/or undifferentiated connective tissue workup to a mesodermal outline. For example, and without limitation, a mesodermal group of a bone and an undifferentiated connective tissue workup including a concentration of serum microRNA of 0.05 nM may relate to a mesodermal outline 116 of reduced binding and support of surrounding tissue. The mesodermal training set may be received as a function of user-entered valuations of mesodermal group, undifferentiated connective tissue workup, and/or mesodermal outline. Computing device 104 may receive mesodermal training by receiving correlations of mesodermal group and/or undifferentiated connective tissue workup that were previously received and/or determined during a previous iteration of determining mesodermal outlines. The mesodermal training set may be received by one or more remote devices that at least correlate a mesodermal group and undifferentiated connective tissue workup to a mesodermal group, wherein a remote device is an external device to computing device 104, as described above. The mesodermal training set may be received in the form of one or more user-entered correlations of a mesodermal group and undifferentiated connective tissue workup to a mesodermal outline. Additionally or alternatively, a user may include an informed advisor, wherein an informed advisor may include, without limitation, rheumatologists, dermatologists, internists, general practitioners, neurologists, pulmonologists, nephrologists, family physicians, and the like thereof.

Still referring to FIG. 1, computing device 104 may receive mesodermal machine-learning model from the remote device that utilizes one or more mesodermal machine learning processes, wherein a remote device is described above in detail. For example, and without limitation, a remote device may include a computing device, external device, processor, and the like thereof. The remote device may perform the mesodermal machine-learning process using the mesodermal training set to generate mesodermal outline 116 and transmit the output to computing device 104. The remote device may transmit a signal, bit, datum, or parameter to computing device 104 that at least relates to ocular profile 116. Additionally or alternatively, the remote device may provide an updated machine-learning model. For example, and without limitation, an updated machine-learning model may be comprised of a firmware update, a software update, a mesodermal machine-learning process correction, and the like thereof. As a non-limiting example a software update may incorporate a new mesodermal group that relates to a modified undifferentiated connective tissue workup. Additionally or alternatively, the updated machine learning model may be transmitted to the remote device, wherein the remote device may replace the machine machine-learning model with the updated machine-learning model and determine the mesodermal outline as a function of the mesodermal group using the updated machine-learning model. The updated machine-learning model may be transmitted by the remote device and received by computing device 104 as a software update, firmware update, or corrected mesodermal machine-learning model. For example, and without limitation a mesodermal machine-learning model may utilize a linear regression machine-learning process, wherein the updated machine-learning model may incorporate a gradient boosting machine-learning process. Updated machine learning model may additionally or alternatively include any machine-learning model used as an updated machine learning model as described in U.S. Non-provisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device 104 may determine mesodermal outline 116 by identifying a connective tissue dysfunction. As used in this disclosure, a "connective tissue dysfunction" is an ailment and/or collection of ailments that impact an individual's connective tissue system. As a non-limiting example, connective tissue dysfunction may include Paget disease of bone, scleroderma, Ehlers-Danlos syndromes, epidermolysis bullosa, Marfan syndrome, osteogenesis imperfecta, polymyositis, dermatomyositis, Sjogren's syndrome, amyopathic dermatomyositis, bizarre parosteal osteochondromatous proliferation, eosinophilic fasciitis, melorheostosis, pacman dysplasia, ribbing disease, twenty-nail dystrophy, Weill-Marchsesani syndrome, worth type autosomal dominant osteosclerosis, and the like thereof. Connective tissue dysfunction may be determined as a function of one or more dysfunction machine-learning models. As used in this disclosure, a "dysfunction machine-learning model" is a machine-learning model to produce a connective tissue dysfunction output given undifferentiated connective tissue workups as inputs; this is in contrast to a non-machine learning software program where the commands to be executed are determined in advance by a user and written in a programming language. Dysfunction machine-learning model may include one or more dysfunction machine-learning processes such as supervised, unsupervised, or reinforcement machine-learning processes that computing device 104 and/or a remote device may or may not use in the determination of connective tissue dysfunction. A dysfunction machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train dysfunction machine-learning process as a function of a dysfunction training set. As used in this disclosure, a "dysfunction training set" is a training set that correlates at least a mesodermal enumeration and a connective tissue system effect to a connective tissue dysfunction. As used in this disclosure, a "mesodermal enumeration" is a measurable value associated with the undifferentiated connective tissue workup. As used in this disclosure, a "connective tissue system effect" is an impact and/or effect on the connective tissue system of an individual. As a non-limiting example a mesodermal enumeration of 23 may be relate to a connective tissue system effect of dry eyes and/or dry mouth, wherein a connective tissue dysfunction of Sjogren's syndrome may be determined. The dysfunction training set may be received as a function of user-entered valuations of mesodermal enumerations, connective tissue system effects, and/or connective tissue dysfunctions. Computing device 104 may receive dysfunction training by receiving correlations of mesodermal enumerations and/or connective tissue system effects that were previously received and/or determined during a previous iteration of determining connective tissue dysfunctions. The dysfunction training set may be received by one or more remote devices that at least correlate a mesodermal enumeration and/or connective tissue system effect to an connective tissue dysfunction, wherein a remote device is an external device to computing device 104, as described above. The dysfunction training set may be received in the form of one or more user-entered correlations of a mesodermal enumeration and connective system effect to a connective tissue dysfunction. Additionally or alternatively, a user may include an informed advisor, wherein an informed advisor may include, without limitation, rheumatologists, dermatologists, internists, general practitioners, neurologists, pulmonologists, nephrologists, family physicians, and the like thereof.

Still referring to FIG. 1, computing device 104 may receive dysfunction machine-learning model from the remote device that utilizes one or more dysfunction machine learning processes, wherein a remote device is described above in detail. For example, and without limitation, a remote device may include a computing device, external device, processor, and the like thereof. The remote device may perform the dysfunction machine-learning process using the dysfunction training set to generate connective tissue dysfunction and transmit the output to computing device 104. The remote device may transmit a signal, bit, datum, or parameter to computing device 104 that at least relates to connective tissue dysfunctions. Additionally or alternatively, the remote device may provide an updated machine-learning model. For example, and without limitation, an updated machine-learning model may be comprised of a firmware update, a software update, a dysfunction machine-learning process correction, and the like thereof. As a non-limiting example a software update may incorporate a new mesodermal enumeration that relates to a modified connective tissue system effect. Additionally or alternatively, the updated machine learning model may be transmitted to the remote device, wherein the remote device may replace the dysfunction machine-learning model with the updated machine-learning model and determine the connective tissue dysfunction as a function of the mesodermal enumeration using the updated machine-learning model. The updated machine-learning model may be transmitted by the remote device and received by computing device 104 as a software update, firmware update, or corrected dysfunction machine-learning model. For example, and without limitation dysfunction machine-learning model may utilize a Naïve bayes machine-learning process, wherein the updated machine-learning model may incorporate decision tree machine-learning process.

Still referring to FIG. 1, computing device 104 generates an outline signature 132 as a function of mesodermal outline 116. As used in this disclosure, an "outline signature" is a quantitative value indicating a severity of mesodermal outline 116. As a non-limiting example outline signature 132 may be 23 for a mesodermal outline associated with cyanosis of fingers during emotional stress. As a further non-limiting example, outline signature 132 may be 73 for a mesodermal outline associated with mixed connective tissue disease. Computing device 104 determines outline signature by receiving a normal range 136. As used in this disclosure, a "normal range" is a reference range and/or reference interval for a normal physiologic measurement of mesodermal outline 116. As a non-limiting example mesodermal outline 116 may identify an Anti-DsDNA concentration of 3.2 IU/mL and/or 0.11 IU/fl. oz., wherein a safe range of Anti-DsDNA concentrations for mixed connective tissue diseases may be 5-9 IU/mL 0.17-0.31 IU/fl. oz. As a further non-limiting example, mesodermal outline 116 may determine a PT/APTT speed of 92 seconds wherein a normal range of PT/APTT may be 30-40 seconds. Normal range 136 is received as a function of a mesodermal guideline 140. As used in this disclosure, a "mesodermal guideline" is a medical guideline for the measurement of connective tissue health status. As a non-limiting example mesodermal guideline 140 may be identified by one or more organizations that relate to, represent, and/or study connective tissue function in humans, such as Connective Tissue Oncology Society, Cedars-Sinai, Association of VA Surgeons, and the like thereof. As a further non-limiting example, mesodermal guideline 140 may determine safe range 136 as a function of one or more medical research journals, such as Connective Tissue Research, Physiology, SCI Journal, The Lancet, New England Journal of Medicine, Science, Journal of the American Medical Association, and the like thereof.

Still referring to FIG. 1, computing device 104 may generate outline signature 132 by determining at least an outline vector as a function of mesodermal outline 116. As used in this disclosure, an "outline vector" is a data structure that represents one or more a quantitative values and/or measures of mesodermal outline 116. A vector may be represented as an n-tuple of values, where n is at least one value, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes. Computing device 104 may generate a degree of variance as a function of the outline vector and normal range. As used in this disclosure, a "degree of variance" is a quantitative value comprising the magnitude of divergence of the outline vector from the normal range. As a non-limiting example, a degree of variance may be 42 for the outline vector associated with an anticardiolipin Ab concentration of 15 units/mL and/or 0.51 units/fl. oz., wherein the normal range is 100-400 units/mL and/or 3.38-13.53 units/fl. oz. Degree of variance may include a transgression parameter. As used in this disclosure, a "transgression parameter" is a parameter that identifies one or more degrees of variance that exceed a variance limit. As a non-limiting example, transgression parameter may determine that a degree of variance exceeded the normal range by 12 for an initial serological evaluation with antinuclear antibody analysis. Outline signature 132 may be determined as a function of the degree of variance and a mesodermal threshold. As used in this disclosure "mesodermal threshold" is a quantitative value associated with the limit that a degree of variance may have. Mesodermal threshold may relate to one or more severities that at least identify a low severity and/or high severity, wherein a severity is a critical and/or dire degree of variance. As a non-limiting example, a mesodermal threshold stating that a degree of variance exceeding 35 for Marfan syndrome may relate to a high severity. As a further non-limiting example, a mesodermal threshold stating that a degree of variance exceeding 12 for polymyositis may relate to a low severity. For example, and without limitation, outline signature 132 may determine a medium severity of reduced structure and support of connective tissue health status due to a degree of variance of 35, wherein a mesodermal threshold is 32.

Still referring to FIG. 1, computing device 104 generates outline signature 132 as a function of normal range 136 and mesodermal outline 116 using a signature machine-learning model. 144. As used in this disclosure, a "signature machine-learning model" is a machine-learning model to produce an outline signature output given a mesodermal outline and/or normal range as inputs; this is in contrast to a non-machine learning software program where the commands to be executed are determined in advance by a user and written in a programming language. Signature machine-learning model 144 may include one or more signature machine-learning processes such as supervised, unsupervised, or reinforcement machine-learning processes that computing device 104 and/or a remote device may or may not use in the determination of outline signature 132. A signature machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train signature machine-learning process as a function of a signature training set. As used in this disclosure, a "signature training set" is a training set that correlates at least mesodermal outline 116 and normal range 136. As a non-limiting example a mesodermal outline of inflammation in the lungs, heart, and inner abdomen and a safe range of 10-50 mL of pericardial fluid may identify an outline signature of 33 for serositis. The signature training set may be received as a function of user-entered valuations of mesodermal outline, normal range, and or signature outline. Computing device 104 may receive signature training by receiving correlations of a mesodermal outline and/pr normal range that were previously received and/or determined during a previous iteration of determining outline signature. The signature training set may be received by one or more remote devices that at least correlate mesodermal outline and/or normal range to signature outline, wherein a remote device is an external device to computing device 104, as described above. The signature training set may be received by one or more user-entered correlations of a mesodermal outline and/or normal range to an outline signature. Additionally or alternatively, a user may include an informed advisor, wherein an informed advisor may include, without limitation, rheumatologists, dermatologists, internists, general practitioners, neurologists, pulmonologists, nephrologists, family physicians, and the like thereof.

Still referring to FIG. 1, computing device 104 may receive signature machine-learning model 144 from the remote device that utilizes one or more signature machine learning processes, wherein a remote device is described above in detail. For example, and without limitation, a remote device may include a computing device, external device, processor, and the like thereof. The remote device may perform the signature machine-learning process using the signature training set to generate outline signature and transmit the output to computing device 104. The remote device may transmit a signal, bit, datum, or parameter to computing device 104 that at least relates to outline signatures. Additionally or alternatively, the remote device may provide an updated machine-learning model. For example, and without limitation, an updated machine-learning model may be comprised of a firmware update, a software update, a signature machine-learning process correction, and the like thereof. As a non-limiting example a software update may incorporate a new mesodermal outline that relates to a modified normal range. Additionally or alternatively, the updated machine learning model may be transmitted to the remote device, wherein the remote device may replace the signature machine-learning model with the updated machine-learning model and determine the outline signature as a function of the mesodermal outline using the updated machine-learning model. The updated machine-learning model may be transmitted by the remote device and received by computing device 104 as a software update, firmware update, or corrected signature machine-learning model. For example, and without limitation procreant machine-learning model may utilize a elasticnet regression machine-learning process, wherein the updated machine-learning model may incorporate random forest regression machine-learning process.

Still referring to FIG. 1, computing device 104 identifies an edible 148 as a function of outline signature 132. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. Computing device 104 may identify edible 148 as a function of obtaining a nourishment composition. As used in this disclosure, a "nourishment composition" is a list and/or compilation of all of the nutrients contained in an edible. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition may be obtained as a function of an edible directory, wherein an edible directory is a database of edibles that may be identified as a function of one or more outline signatures, as described in detail below, in reference to FIG. 3.

Still referring to FIG. 1, computing device 104 may identify edible 148 as a function of nourishment composition, outline signature 132, and an edible machine-learning model. As used in this disclosure, an "edible machine-learning model" is a machine-learning model to produce an edible output given nourishment compositions and outline signatures as inputs; this is in contrast to a non-machine learning software program where the commands to be executed are determined in advance by a user and written in a programming language. Edible machine-learning model may include one or more edible machine-learning processes such as supervised, unsupervised, or reinforcement machine-learning processes that computing device 104 and/or a remote device may or may not use in the determination of edible 148. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure, an "edible training set" is a training set that correlates at least nourishment composition and outline signature 132 to an edible. For example, and without limitation, nourishment composition of 1000 ng/mL of vitamin C and an outline signature of 30 for mixed connective tissue disease may relate to an edible of oranges. The edible training set may be received as a function of user-entered valuations of nourishment compositions, outline signatures, and/or edibles. Computing device 104 may receive edible training by receiving correlations of nourishment compositions and/or outline signatures that were previously received and/or determined during a previous iteration of determining edibles. The edible training set may be received by one or more remote devices that at least correlate a nourishment composition and outline signature to an edible, wherein a remote device is an external device to computing device 104, as described above. The edible training set may be received by one or more user-entered correlations of a nourishment composition and outline signature to an edible. Additionally or alternatively, a user may include an informed advisor, wherein an informed advisor may include, without limitation, rheumatologists, dermatologists, internists, general practitioners, neurologists, pulmonologists, nephrologists, family physicians, and the like thereof.

Still referring to FIG. 1, edible machine-learning model may identify edible 148 as a function of one or more classifiers. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn as a function of a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may receive edible machine-learning model from the remote device that utilizes one or more edible machine learning processes, wherein a remote device is described above in detail. For example, and without limitation, a remote device may include a computing device, external device, processor, and the like thereof. The remote device may perform the edible machine-learning process using the edible training set to generate edible 148 and transmit the output to computing device 104. The remote device may transmit a signal, bit, datum, or parameter to computing device 104 that at least relates to edible 148. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified outline signature. Additionally or alternatively, the updated machine learning model may be transmitted to the remote device, wherein the remote device may replace the edible machine-learning model with the updated machine-learning model and determine the edible as a function of the outline signature using the updated machine-learning model. The updated machine-learning model may be transmitted by the remote device and received by computing device 104 as a software update, firmware update, or corrected edible machine-learning model. For example, and without limitation an edible machine-learning model may utilize a decision tree machine-learning process, wherein the updated machine-learning model may incorporate a logistic regression machine-learning process. Updated machine learning model may additionally or alternatively include any machine-learning model used as an updated machine learning model as described in U.S. Nonprovisional application Ser. No. 17/106,658.

Still referring to FIG. 1, computing device 104 may identify edible 148 as a function of a likelihood parameter. As used in this disclosure, a "likelihood parameter" is a parameter that identifies the probability of a user to consume an edible. As a non-limiting example likelihood parameter may identify a high probability that a user will consume an edible of steak. As a further non-limiting example likelihood parameter may identify a low probability that a user will consume an edible of potatoes. Likelihood parameter may be determined as a function of a user taste profile. As used in this disclosure, a "user taste profile" is a profile of a user that identifies one or more desires, preferences, wishes, and/or wants that a user has. As a non-limiting example a user taste profile may include a user's preference for salmon flavor and/or hard textured edibles. Likelihood parameter may be determined as a function of an edible profile. As used in this disclosure, an "edible profile" is taste of an edible is the sensation of flavor perceived in the mouth and throat on contact with the edible. Edible profile may include one or more flavor variables. As used in this disclosure, a "flavor variable" is a variable associated with the distinctive taste of an edible, wherein a distinctive taste may include, without limitation sweet, bitter, sour, salty, umami, cool, and/or hot. Edible profile may be determined as a function of receiving flavor variable as a function of a flavor directory. As used in this disclosure, a "flavor directory" is a database of flavors for an edible. As a non-limiting example flavor directory may include a list and/or collection of edibles that all contain sweet flavor variables. As a further non-limiting example flavor directory may include a list and/or collection of edibles that all contain salty flavor variables. Likelihood parameter may alternatively or additionally include any user taste profile and/or edible profile used as a likelihood parameter as described in U.S. Nonprovisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 outputs a nourishment program 152 of a plurality of nourishment programs as a function of edible 148. As used in this disclosure, a "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 152 may consist of recommending steak for 2 days. As a further non-limiting example nourishment program 152 may recommend tofu for a first day, ice cream for a second day, and bacon for a third day. Nourishment program 152 may include one or more diet programs such as paleo, keto, vegan, vegetarian, and the like thereof. Computing device 104 outputs nourishment program as a function of a mesodermal outcome. As used in this disclosure, a "mesodermal outcome" is an outcome that an edible may generate according to a predicted and/or purposeful plan. As a non-limiting example, mesodermal outcome may include a treatment outcome. As used in this disclosure, a "treatment outcome" is an intended outcome that is designed to at least reverse and/or eliminate outline signature 132 associated with mesodermal outline 116 and/or mesodermal dysfunction. As a non-limiting example, a treatment outcome may include reversing the effects of the mesodermal dysfunction of polymyotitis. As a further non-limiting example, a treatment outcome includes reversing the mesodermal dysfunction of epidermolysis bullosa. Mesodermal outcome may include a prevention outcome. As used in this disclosure, a "prevention outcome" is an intended outcome that is designed to at least prevent and/or avert outline signature 132 associated with mesodermal outline 116 and/or mesodermal dysfunction. As a non-limiting example, a prevention outcome may include preventing the development of the mesodermal dysfunction of scleroderma.

Still referring to FIG. 1, computing device 104 may output nourishment program 152 function of edible 148 and mesodermal outcome using a nourishment machine-learning model. As used in this disclosure, a "nourishment machine-learning model" is a machine-learning model to produce a nourishment program output given edibles and/or mesodermal outcomes as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the determination of nourishment program 152. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates a mesodermal outcome to an edible. The nourishment training set may be received as a function of user-entered edibles, mesodermal outcomes, and/or nourishment programs. Computing device 104 may receive nourishment training by receiving correlations of mesodermal outcomes and/or edibles that were previously received and/or determined during a previous iteration of outputting nourishment programs. The nourishment training set may be received by one or more remote devices that at least correlate a mesodermal outcome and/or edible to a nourishment program, wherein a remote device is an external device to computing device 104, as described above. The nourishment training set may be received by one or more user-entered correlations of a mesodermal outcome and edible to a nourishment program. Additionally or alternatively, a user may include an informed advisor, wherein an informed advisor may include, without limitation, rheumatologists, dermatologists, internists, general practitioners, neurologists, pulmonologists, nephrologists, family physicians, and the like thereof.

Still referring to FIG. 1, computing device 104 may receive the nourishment machine-learning model from the remote device that utilizes one or more nourishment machine learning processes, wherein a remote device is described above in detail. For example, and without limitation, a remote device may include a computing device, external device, processor, and the like thereof. The remote device may perform the nourishment machine-learning process using the nourishment training set to output nourishment program 152 and transmit the output to computing device 104. The remote device may transmit a signal, bit, datum, or parameter to computing device 104 that at least relates to nourishment program 152. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new mesodermal outcome that relates to a modified edible. Additionally or alternatively, the updated machine learning model may be transmitted to the remote device, wherein the remote device may replace the nourishment machine-learning model with the updated machine-learning model and output the nourishment program as a function of the mesodermal outcome using the updated machine-learning model. The updated machine-learning model may be transmitted by the remote device and received by computing device 104 as a software update, firmware update, or corrected nourishment machine-learning model. For example, and without limitation the nourishment machine-learning model may utilize a heuristic algorithm machine-learning process, wherein the updated machine-learning model may incorporate nearest neighbor machine-learning processes.

Figure 2:
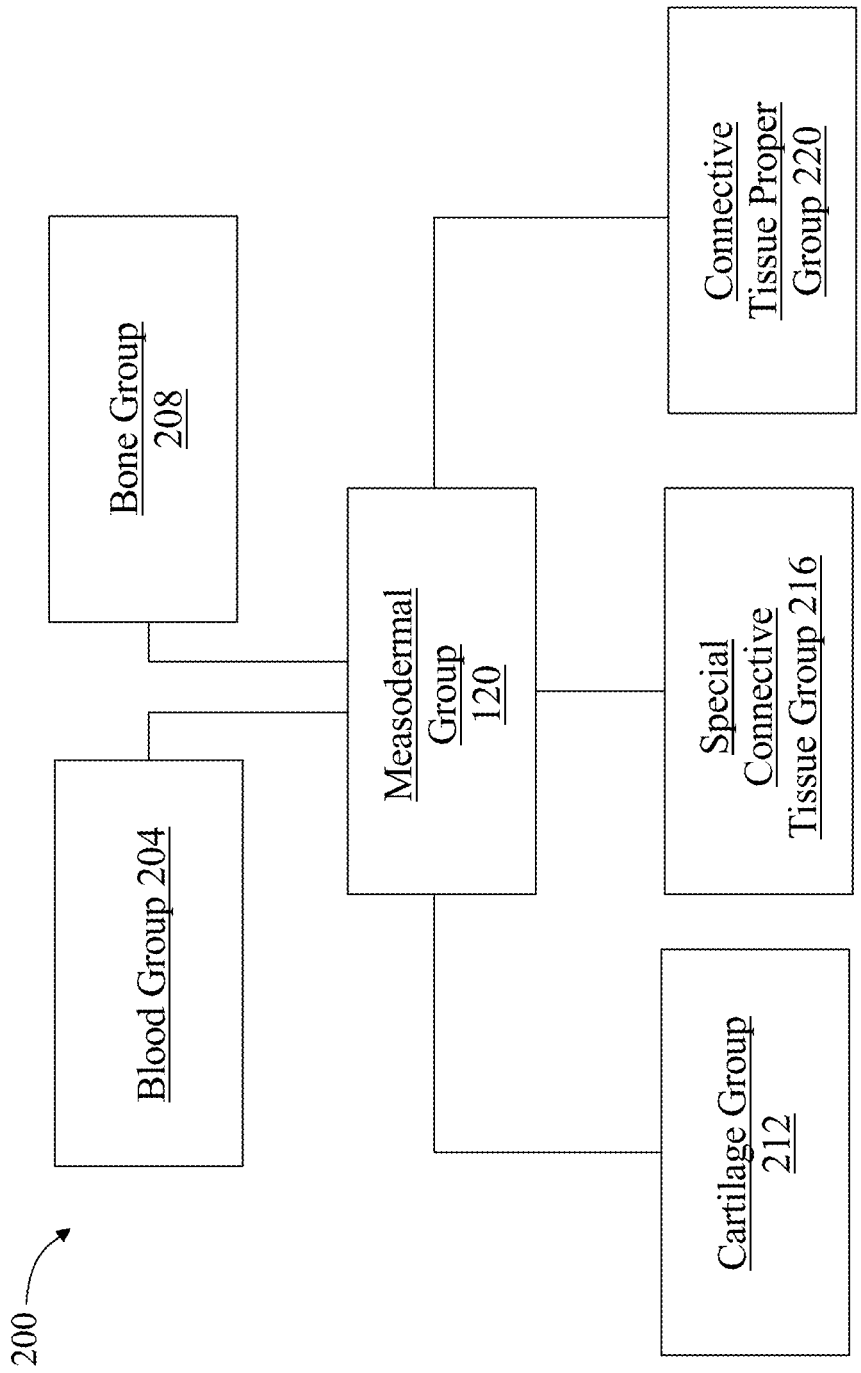
FIG. 2 is a block diagram of an exemplary embodiment of a mesodermal group according to an embodiment of the invention.

Now referring to FIG. 2, an exemplary embodiment 200 of mesodermal group 120. Mesodermal group 120 may include a blood group 204. As used in this disclosure, a "blood group" is connective tissue containing a group of living cell types and/or matrix surrounding living cell types. As a non-limiting example blood group 204 may include red blood cells, erythrocytes, white blood cells, leukocytes, plasma, lymphocytes, cytoplasmic fragments, platelets, thrombocytes, and the like thereof. Mesodermal group 120 may include a bone group 208. As used in this disclosure, a "bone group" is a group of connective tissue that has a large amount of two different types of matrix material consisting of collagen and/or elastic fibers as well as mineral salts, such as calcium. As a non-limiting example bone group 208 may include osteoblast groups, osteocyte groups, osteoclast groups, compact groups, spongy groups, and the like thereof. Mesodermal group 120 may include a cartilage group 212. As used in this disclosure, a "cartilage group" is a group of connective tissue that is composed of specialist chondroblasts, wherein the specialist chondroblasts are flexible and lack blood vessels. As a non-limiting example cartilage group 212 may include elastic cartilage, hyaline cartilage, fibrocartilage and the like thereof. Mesodermal group 120 may include a special connective tissue group 216. As used in this disclosure, a "special connective tissue group" is a group of connective tissue that is composed of specific tissues for a particular function and/or area of the human body. As a non-limiting example special connective tissue group 216 may include reticular connective tissue groups, adipose tissue groups an osseous tissue, and the like thereof. Mesodermal group 120 may include a connective tissue proper group 220. As used in this disclosure a "connective tissue proper group" is a group of connective tissue that is composed of loose and/or dense connective tissue, wherein loose and/or dense connective tissue is distinguished by the ratio of ground substance to fibrous tissue. As a non-limiting example connective tissue proper group 220 may include tendon groups, ligament groups, dense regular groups, dense irregular groups, elastic groups, and the like thereof.

Figure 3:
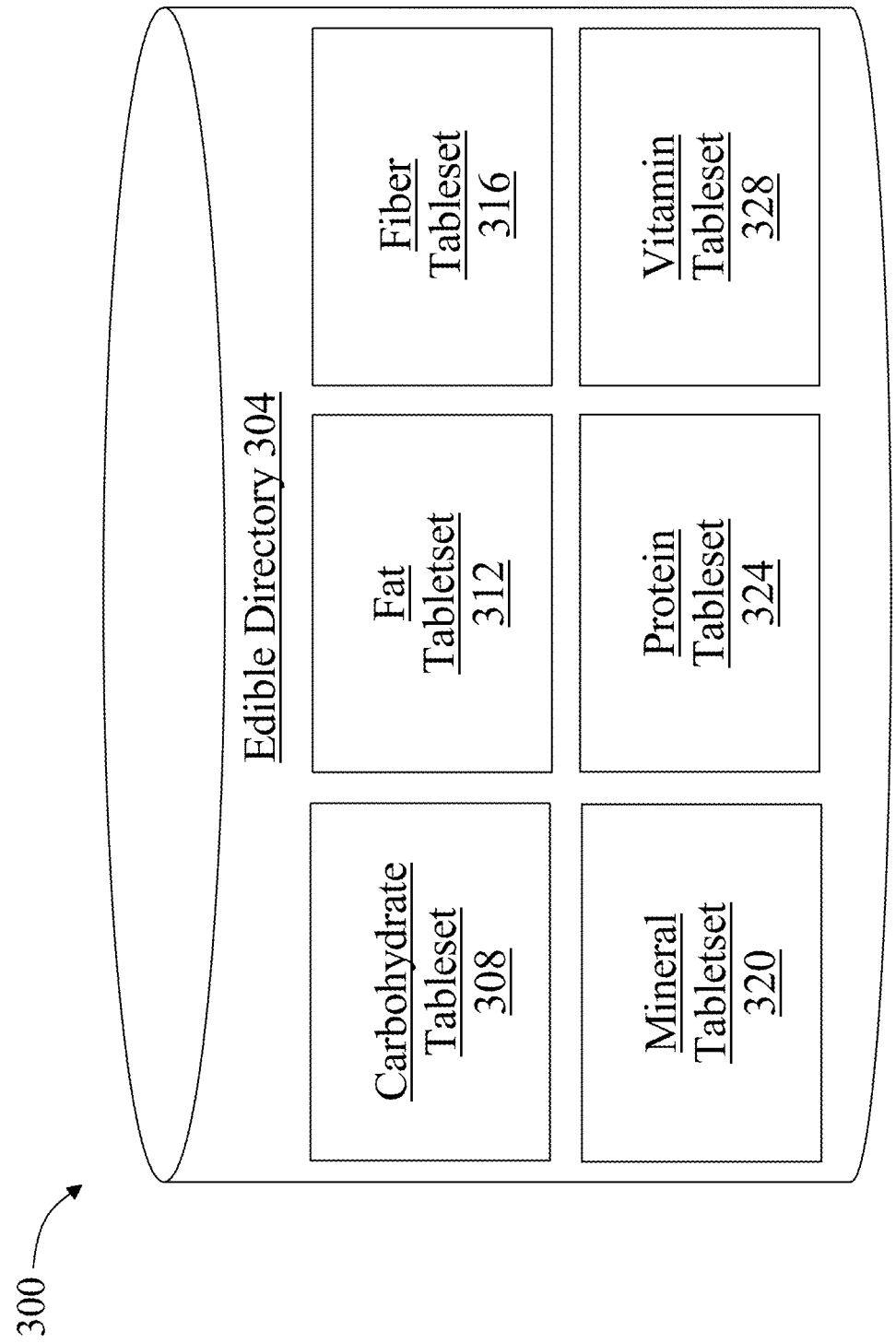
FIG. 3 is a block diagram of an exemplary embodiment of an edible directory according to an embodiment of the invention.

Now referring to FIG. 3, an exemplary embodiment 300 of an edible directory 304 according to an embodiment of the invention is illustrated. Edible directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 304 may alternatively or additionally be implemented using a distributed data storage protocol and/or data structure, such as a distributed hash table or the like. Edible directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 304 may include a carbohydrate tableset 308. Carbohydrate tableset 308 may relate to a nourishment composition of an edible with respect to the quantity and/or type of carbohydrates in the edible. As a non-limiting example, carbohydrate tableset 308 may include monosaccharides, disaccharides, oligosaccharides, polysaccharides, and the like thereof. Edible directory 304 may include a fat tableset 312. Fat tableset 312 may relate to a nourishment composition of an edible with respect to the quantity and/or type of esterified fatty acids in the edible. Fat tableset 312 may include, without limitation, triglycerides, monoglycerides, diglycerides, phospholipids, sterols, waxes, and free fatty acids. Edible directory 304 may include a fiber tableset 316. Fiber tableset 316 may relate to a nourishment composition of an edible with respect to the quantity and/or type of fiber in the edible. As a non-limiting example, fiber tableset 316 may include soluble fiber, such as beta-glucans, raw guar gum, *psyllium*, inulin, and the like thereof as well as insoluble fiber, such as wheat bran, cellulose, lignin, and the like thereof. Edible directory 304 may include a mineral tableset 320. Mineral tableset 320 may relate to a nourishment composition of an edible with respect to the quantity and/or type of minerals in the edible. As a non-limiting example, mineral tableset 320 may include calcium, phosphorous, magnesium, sodium, potassium, chloride, sulfur, iron, manganese, copper, iodine, zing, cobalt, fluoride, selenium, and the like thereof. Edible directory 304 may include a protein tableset 324. Protein tableset 324 may relate to a nourishment composition of an edible with respect to the quantity and/or type of proteins in the edible. As a non-limiting example, protein tableset 324 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 304 may include a vitamin tableset 328. Vitamin tableset 328 may relate to a nourishment composition of an edible with respect to the quantity and/or type of vitamins in the edible. As a non-limiting example, vitamin tableset 328 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
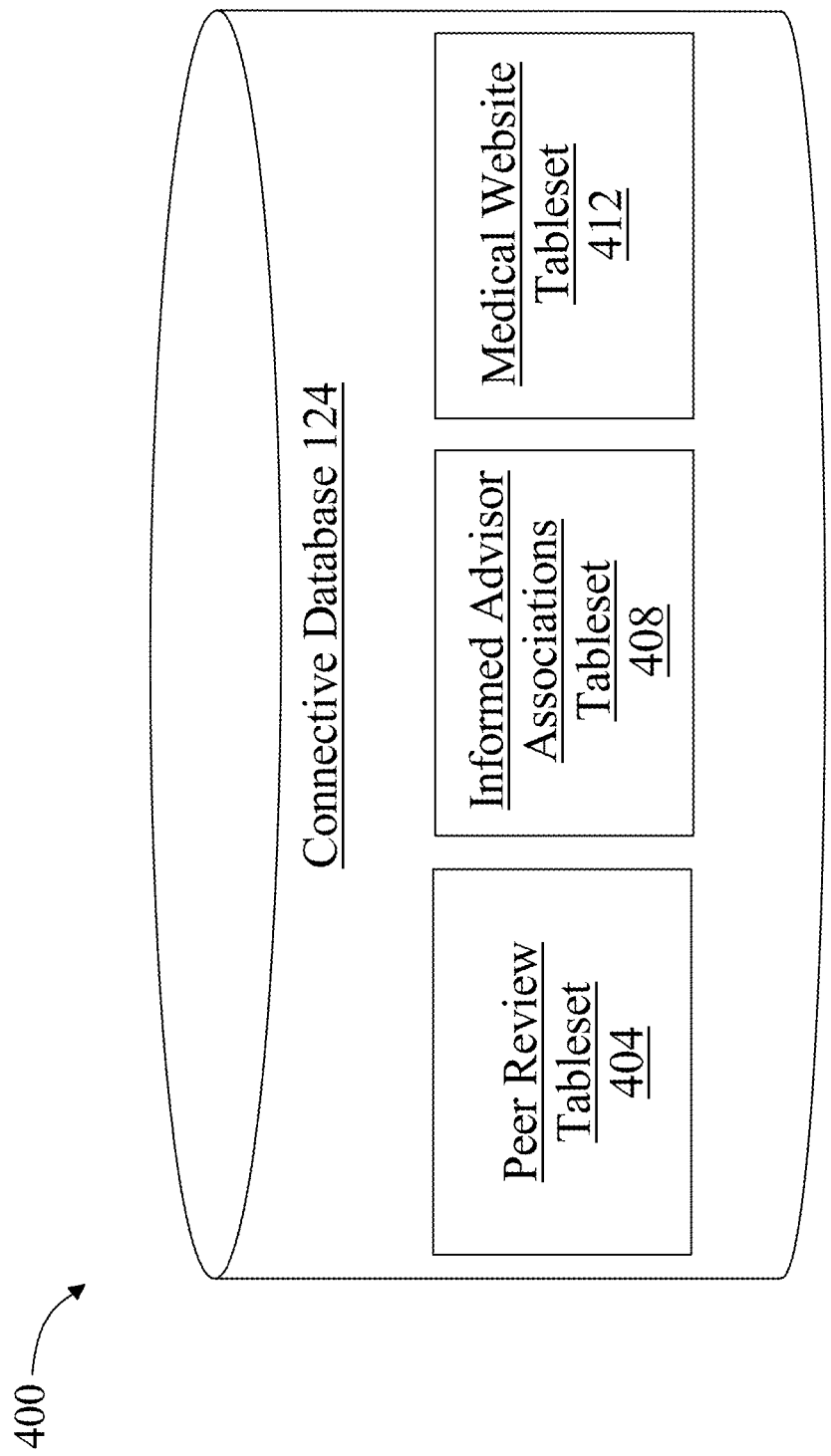
FIG. 4 is a block diagram of an exemplary embodiment of a connective database according to an embodiment of the invention.

Now referring to FIG. 4, an exemplary embodiment 300 of a connective database 124 according to an embodiment of the invention is illustrated. Connective database 124 may be implemented, without limitation, as a relational databank, a key-value retrieval databank such as a NOSQL databank, or any other format or structure for use as a databank that a person skilled in the art would recognize as suitable upon review of the entirety of this disclosure. Connective database 124 may alternatively or additionally be implemented using a distributed data storage protocol and/or data structure, such as a distributed hash table or the like. Connective database 124 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Connective database 124 may include a peer review tableset 404. Peer review tableset 404 may identify one or more mesodermal groups as a function of a peer review evaluation conducted by one or more people with similar competencies. As a non-limiting example peer review tableset 404 may include professional peer reviews, scholarly peer reviews, government peer reviews, medical peer reviews, technical peer reviews, and the like thereof. Connective database 124 may include an informed advisor associations tableset 408. Informed advisor associations tableset 408 may identify one or more mesodermal groups as a function of one or more committees, organizations, and/or groups that at least determine and/or organize mesodermal groups. As a non-limiting example informed advisor association tableset 408 may include the American Medical Association, Connective Tissue Oncology Society, Association of Autoimmune Connective Tissue Disease, National Institute of Arthritis and Musculoskeletal and Skin Diseases, and the like thereof. Connective database 124 may include a medical website tableset 412. Medical website tableset 412 may identify one or more mesodermal groups as a function of one or more online and/or web-based medical recommendations. As a non-limiting example medical website tableset 412 may include Medline Plus, Drugs.com, Mayo Clinic, Orphanet, Medgadget, WebMD, Health.gov, SPM ePatients blog, and the like thereof.

Figure 5:
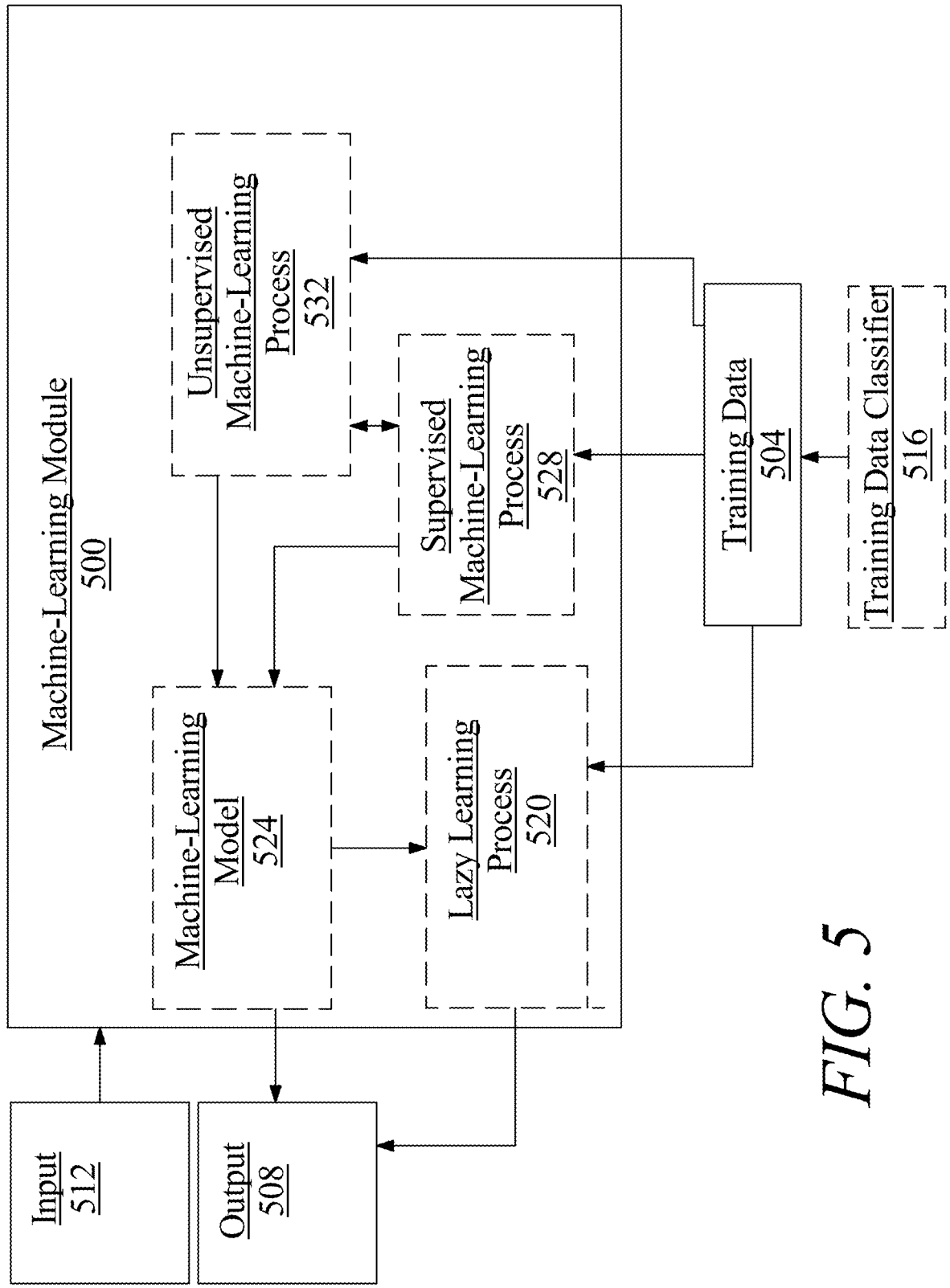
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs of mesodermal groups and undifferentiated connective tissue workups may be used to output a mesodermal outline.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories of mesodermal groups such as cartilage groups, blood groups, connective tissue proper groups, special connective tissue groups, and the like thereof as described above, in reference to FIG. 2.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include mesodermal groups and undifferentiated connective tissue workups as described above as inputs, mesodermal outlines as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
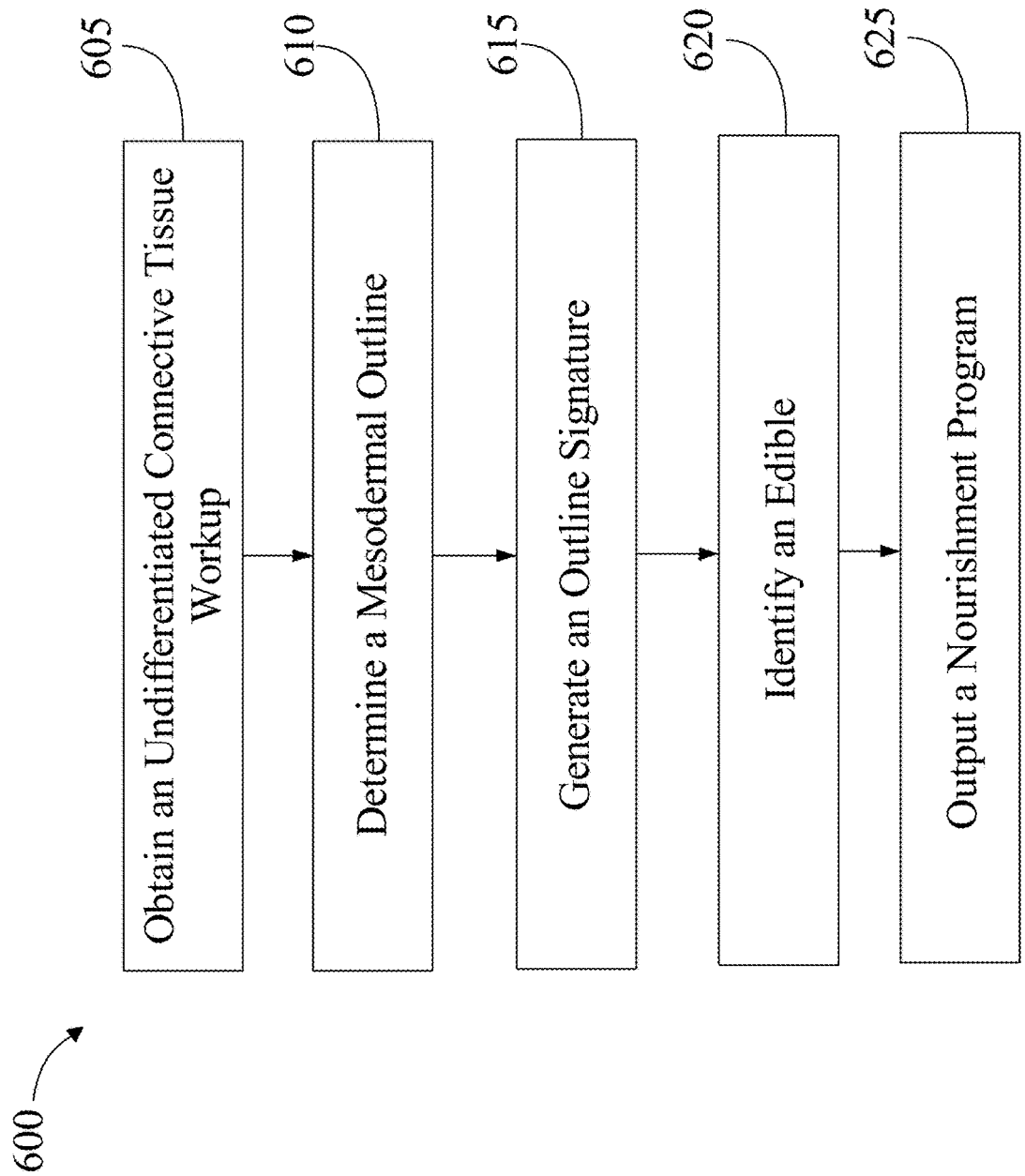
FIG. 6 is a process flow diagram illustrating an exemplary embodiment of a method of generating a mesodermal outline nourishment program.

Now referring to FIG. 6, an exemplary embodiment of a method 600 for generating a mesodermal outline nourishment program is illustrated. At step 605, a computing device 104 obtains at least an undifferentiated connective tissue workup 108 as a function of a procreant system 112. Computing device 104 includes any of the computing device 104 as described above, in reference to FIGS. 1-5. Undifferentiated connective tissue workup 108 includes any of the undifferentiated connective tissue workup as described above, in reference to FIGS. 1-5. Connective tissue system 112 includes any of the connective tissue 112 as described above, in reference to FIGS. 1-5.

Still referring to FIG. 6, at step 610, computing device 104 determines a mesodermal outline 116 as a function of undifferentiated connective tissue workup 108. Mesodermal outline 116 includes any of the mesodermal outline 116 as described above, in reference to FIGS. 1-5. Computing device 104 obtains a mesodermal group 120 as a function of a connective database 124. Mesodermal group 120 includes any of the mesodermal group 120 as described above, in reference to FIGS. 1-5. Connective database 124 includes any of the connective database 124 as described above, in reference to FIGS. 1-5. Computing device 104 determines mesodermal outline 116 as a function of mesodermal group 120 and undifferentiated connective tissue workup 108 using a mesodermal machine-learning model 128. Mesodermal machine-learning model 128 includes any of the mesodermal machine-learning model 128 as described above, in reference to FIGS. 1-5.

Still referring to FIG. 6, at step 615, computing device 104 generates an outline signature 132 as a function of mesodermal outline 116. Outline signature 132 includes any of the outline signature 132 as described above, in reference to FIGS. 1-5. Computing device 104 receives a normal range 136 as a function of a mesodermal guideline 140. Normal range 136 includes any of the normal range 136 as described above, in reference to FIGS. 1-5. Mesodermal guideline 140 includes any of the mesodermal guideline 140 as described above, in reference to FIGS. 1-5. Computing device 104 generates outline signature 132 as a function of normal range 136 and mesodermal guideline 140 using a signature machine-learning model 144. Signature machine-learning model 144 includes any of the signature machine-learning model 144 as described above, in reference to FIGS. 1-5.

Still referring to FIG. 6, at step 620, computing device 104 identifies at least an edible 148 as a function of outline signature 132. Edible 148 includes any of the edible 148 as described above, in reference to FIGS. 1-5.

Still referring to FIG. 6, at step 625, computing device 104, outputs a nourishment program 152 of a plurality of nourishment programs as a function of edible 148. Nourishment program 152 includes any of the nourishment program 152 as described above, in reference to FIGS. 1-5.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 7:
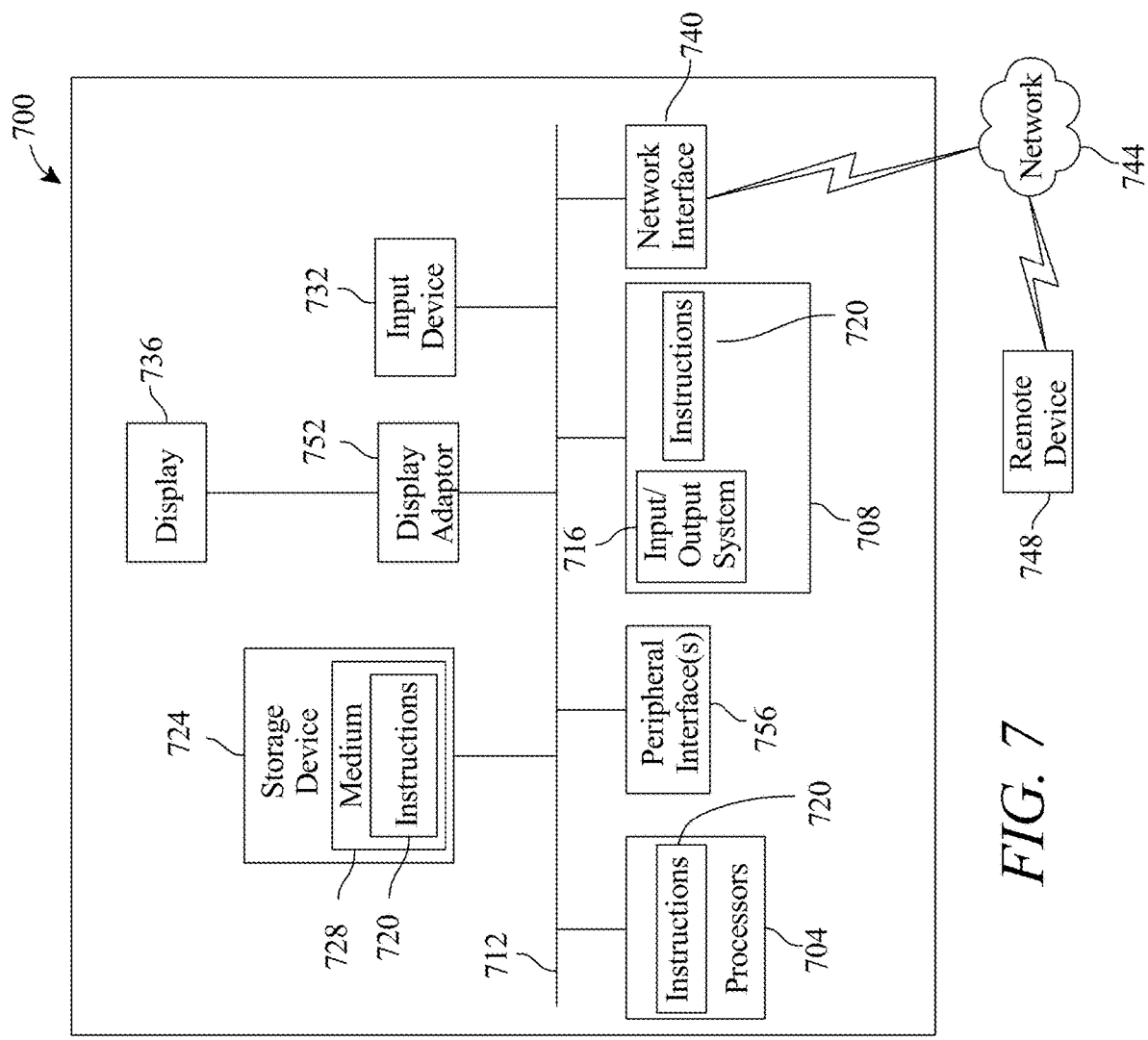
FIG. 7 is a block diagram of a computing system that can be used to implement any one or more of the methodologies disclosed herein and any one or more portions thereof.

FIG. 7 shows a diagrammatic representation of one embodiment of a computing device in the exemplary form of a computer system 700 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 700 includes a processor 704 and a memory 708 that communicate with each other, and with other components, via a bus 712. Bus 712 may include any of several types of bus structures including, but not limited to, a memory bus, a memory controller, a peripheral bus, a local bus, and any combinations thereof, using any of a variety of bus architectures.

Processor 704 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 704 may be organized according to Von Neumann and/or Harvard architecture as a non-limiting example. Processor 704 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 708 may include various components (e.g., machine-readable media) including, but not limited to, a random-access memory component, a read only component, and any combinations thereof. In one example, a basic input/output system 716 (BIOS), including basic routines that help to transfer information between elements within computer system 700, such as during start-up, may be stored in memory 708. Memory 708 may also include (e.g., stored on one or more machine-readable media) instructions (e.g., software) 720 embodying any one or more of the aspects and/or methodologies of the present disclosure. In another example, memory 708 may further include any number of program modules including, but not limited to, an operating system, one or more application programs, other program modules, program data, and any combinations thereof.

Computer system 700 may also include a storage device 724. Examples of a storage device (e.g., storage device 724) include, but are not limited to, a hard disk drive, a magnetic disk drive, an optical disc drive in combination with an optical medium, a solid-state memory device, and any combinations thereof. Storage device 724 may be connected to bus 712 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 724 (or one or more components thereof) may be removably interfaced with computer system 700 (e.g., via an external port connector (not shown)). Particularly, storage device 724 and an associated machine-readable medium 728 may provide nonvolatile and/or volatile storage of machine-readable instructions, data structures, program modules, and/or other data for computer system 700. In one example, software 720 may reside, completely or partially, within machine-readable medium 728. In another example, software 720 may reside, completely or partially, within processor 704.

Computer system 700 may also include an input device 732. In one example, a user of computer system 700 may enter commands and/or other information into computer system 700 via input device 732. Examples of an input device 732 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 732 may be interfaced to bus 712 via any of a variety of interfaces (not shown) including, but not limited to, a serial interface, a parallel interface, a game port, a USB interface, a FIREWIRE interface, a direct interface to bus 712, and any combinations thereof. Input device 732 may include a touch screen interface that may be a part of or separate from display 736, discussed further below. Input device 732 may be utilized as a user selection device for selecting one or more graphical representations in a graphical interface as described above.

A user may also input commands and/or other information to computer system 700 via storage device 724 (e.g., a removable disk drive, a flash drive, etc.) and/or network interface device 740. A network interface device, such as network interface device 740, may be utilized for connecting computer system 700 to one or more of a variety of networks, such as network 744, and one or more remote devices 748 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 744, may employ a wired and/or a wireless mode of communication. In general, any network topology may be used. Information (e.g., data, software 720, etc.) may be communicated to and/or from computer system 700 via network interface device 740.

Computer system 700 may further include a video display adapter 752 for communicating a displayable image to a display device, such as display device 736. Examples of a display device include, but are not limited to, a liquid crystal display (LCD), a cathode ray tube (CRT), a plasma display, a light emitting diode (LED) display, and any combinations thereof. Display adapter 752 and display device 736 may be utilized in combination with processor 704 to provide graphical representations of aspects of the present disclosure. In addition to a display device, computer system 700 may include one or more other peripheral output devices including, but not limited to, an audio speaker, a printer, and any combinations thereof. Such peripheral output devices may be connected to bus 712 via a peripheral interface 756. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a mesodermal outline nourishment program, the system comprising:
   a computing device, the computing device configured to:
   obtain at least an undifferentiated connective tissue workup as a function of a connective tissue system;
   determine a mesodermal outline as a function of the undifferentiated connective tissue workup, wherein determining comprises:
   obtaining a mesodermal group as a function of a connective database; and
   determining the mesodermal outline as a function of the mesodermal group and undifferentiated connective tissue workup using a mesodermal machine-learning model, wherein the mesodermal machine-learning model is configured to output the mesodermal outline given the mesodermal group and the undifferentiated connective tissue workup as inputs;

generate an outline signature as a function of the mesodermal outline, wherein generating comprises:
receiving a normal range as a function of a mesodermal guideline; and
generating the outline signature as a function of the normal range and the mesodermal guideline using a signature machine-learning model, wherein the signature machine-learning model is configured to output the outline signature given the mesodermal outline as an input as a function of a signature training set, wherein the signature training set correlates the mesodermal outline to the normal range;

identify an edible as a function of the outline signature; and output a nourishment program of a plurality of nourishment programs as a function of the edible.

2. The system of claim 1, wherein obtaining the at least an undifferentiated connective tissue workup includes receiving a biomarker and obtaining the at least an undifferentiated connective tissue workup as a function of the biomarker.

3. The system of claim 1, wherein obtaining the at least an undifferentiated connective tissue workup includes receiving a mesodermal diagnostic input and obtaining the at least an undifferentiated connective tissue workup as a function of the mesodermal diagnostic input.

4. The system of claim 1, wherein determining the mesodermal outline includes identifying a connective tissue dysfunction and determining the mesodermal outline as a function of the connective tissue dysfunction.

5. The system of claim 4, wherein identifying the connective tissue dysfunction further comprises:
obtaining a dysfunction training set that relates a connective tissue impact and mesodermal enumeration; and
determining the connective tissue dysfunction as a function of the undifferentiated connective tissue workup using a dysfunction machine-learning model, wherein the dysfunction machine-learning model is trained as a function of the dysfunction training set.

6. The system of claim 1, wherein generating the outline signature further comprises:
determining a degree of variance for the mesodermal outline; and
determining the outline signature as a function of the degree of variance and a mesodermal threshold.

7. The system of claim 1, wherein identifying the edible further comprises:
obtaining a nourishment composition from an edible directory; and
identifying an edible using the nourishment composition.

8. The system of claim 1, wherein identifying the edible further comprises:
determining a likelihood parameter, wherein the likelihood parameter relates a user taste profile to an edible profile; and
identifying the edible as a function of the likelihood parameter.

9. The system of claim 8, wherein determining the edible profile further comprises receiving a flavor variable from a flavor directory and determining the edible profile as a function of the flavor variable.

10. The system of claim 1, wherein outputting the nourishment program further comprises:
obtaining a mesodermal outcome; and
outputting the nourishment program as a function of the edible and mesodermal outcome using a nourishment machine-learning model.

11. A method for generating a mesodermal outline nourishment program, the method comprising:
obtaining, by a computing device, at least an undifferentiated connective tissue workup as a function of a connective tissue system;
determining, by the computing device, a mesodermal outline as a function of the undifferentiated connective tissue workup, wherein determining comprises:
obtaining a mesodermal group as a function of a connective database; and
determining the mesodermal outline as a function of the mesodermal group and undifferentiated connective tissue workup using a mesodermal machine-learning model, wherein the mesodermal machine-learning model is configured to output the mesodermal outline given the mesodermal group and the undifferentiated connective tissue workup as inputs;
generating, by the computing device, an outline signature as a function of the mesodermal outline, wherein generating comprises:
receiving a normal range as a function of a mesodermal guideline; and
generating the outline signature as a function of the normal range and the mesodermal guideline using a signature machine-learning model, wherein the signature machine-learning model is configured to output the outline signature given the mesodermal outline as an input as a function of a signature training set, wherein the signature training set correlates the mesodermal outline to the normal range;
identifying, by the computing device, an edible as a function of the outline signature; and
outputting, by the computing device, a nourishment program of a plurality of nourishment programs as a function of the edible.

12. The method of claim 11, wherein obtaining the at least an undifferentiated connective tissue workup includes receiving a biomarker and obtaining the at least an undifferentiated connective tissue workup as a function of the biomarker.

13. The method of claim 11, wherein obtaining the at least an undifferentiated connective tissue workup includes receiving a mesodermal diagnostic input from an informed advisor and obtaining the at least an undifferentiated connective tissue workup as a function of the mesodermal diagnostic input.

14. The method of claim 11, wherein determining the mesodermal outline includes identifying a connective tissue dysfunction and determining the mesodermal outline as a function of the connective tissue dysfunction.

15. The method of claim 14, wherein identifying the connective tissue dysfunction further comprises:
obtaining a dysfunction training set that relates a connective tissue impact and mesodermal enumeration; and
determining the connective tissue dysfunction as a function of the undifferentiated connective tissue workup using a dysfunction machine-learning model, wherein the dysfunction machine-learning model is trained as a function of the dysfunction training set.

16. The method of claim 11, wherein generating the outline signature further comprises:
   determining a degree of variance for the mesodermal outline; and
   determining the outline signature as a function of the degree of variance and a mesodermal threshold.

17. The method of claim 11, wherein identifying the edible further comprises:
   obtaining a nourishment composition from an edible directory; and
   identifying an edible using the nourishment composition.

18. The method of claim 11, wherein identifying the edible further comprises:
   determining a likelihood parameter, wherein the likelihood parameter relates a user taste profile to an edible profile; and
   identifying the edible as a function of the likelihood parameter.

19. The method of claim 18, wherein determining the edible profile further comprises receiving a flavor variable from a flavor directory and determining the edible profile as a function of the flavor variable.

20. The method of claim 11, wherein outputting the nourishment program further comprises:
   obtaining a mesodermal outcome; and
   outputting the nourishment program as a function of the edible and mesodermal outcome using a nourishment machine-learning model.

\* \* \* \* \*